(12) United States Patent
Etchells

(10) Patent No.: US 8,134,041 B2
(45) Date of Patent: Mar. 13, 2012

(54) STABILIZED FOAM FOR MEDICAL PSA SUBSTRATE

(76) Inventor: Marc D. Etchells, Florence, MA (US)

( * ) Notice: Subject to any disclaimer, the term of this patent is extended or adjusted under 35 U.S.C. 154(b) by 199 days.

(21) Appl. No.: 12/456,182

(22) Filed: Jun. 12, 2009

(65) Prior Publication Data

US 2009/0258059 A1 Oct. 15, 2009

Related U.S. Application Data

(63) Continuation of application No. 11/152,321, filed on Jun. 14, 2005, now abandoned.

(60) Provisional application No. 60/579,411, filed on Jun. 14, 2004.

(51) Int. Cl.
*A61F 13/00* (2006.01)

(52) U.S. Cl. .............................. 602/42; 602/43; 602/46

(58) Field of Classification Search .............. 602/41–59; 604/304–308; 424/443–449
See application file for complete search history.

(56) References Cited

U.S. PATENT DOCUMENTS

| | | | |
|---|---|---|---|
| 3,930,102 A | 12/1975 | Muller et al. ................. | 428/354 |
| 4,358,489 A | 11/1982 | Green ............................ | 428/31 |
| 4,714,716 A | 12/1987 | Park ................................. | 521/80 |
| 4,773,408 A * | 9/1988 | Cilento et al. .................. | 602/49 |
| 5,254,644 A | 10/1993 | Kobori et al. .................. | 525/478 |
| 5,540,922 A * | 7/1996 | Fabo ............................. | 424/402 |
| 5,780,048 A * | 7/1998 | Lee ............................... | 424/443 |
| 6,042,845 A * | 3/2000 | Sun et al. ...................... | 424/446 |
| 6,280,840 B1 | 8/2001 | Luhmann et al. ............. | 428/343 |
| 6,566,575 B1 * | 5/2003 | Stickels et al. ................. | 602/41 |
| 2003/0101885 A1 | 6/2003 | Jordan et al. .................. | 101/395 |
| 2003/0105176 A1 | 6/2003 | Haas et al. ..................... | 521/179 |
| 2005/0278039 A1 * | 12/2005 | Nobbe ............................ | 623/31 |

FOREIGN PATENT DOCUMENTS

JP 08-239632 9/1996

* cited by examiner

*Primary Examiner* — Patricia Bianco
*Assistant Examiner* — Ophelia Hawthorne
(74) *Attorney, Agent, or Firm* — Ohlandt, Greeley, Ruggiero & Perle, LLP

(57) ABSTRACT

The present invention provides a method for using a stabilized foam that is a crosslinked, closed cell polyolefin having a stabilizing layer and an adhesive layer. The method can be used for treating a wound, scrape, abrasion or skin puncture, for maintaining cleanliness of an operation incision site, suture site, catheter insertion site, or an intentional skin breach site, for monitoring electrical impulses during an EKG or for delivering electrical impulses in TENS or biofeedback therapy, and for reducing scar formation by softening collagen deposits.

25 Claims, No Drawings

STABILIZED FOAM FOR MEDICAL PSA SUBSTRATE

CROSS-REFERENCE TO RELATED APPLICATIONS

The present application is a Continuation of U.S. patent application Ser. No. 11/152,321, filed on Jun. 14, 2005 now abandoned, which claims benefit of U.S. Provisional Patent Application No. 60/579,411, filed on Jun. 14, 2004.

BACKGROUND OF THE INVENTION

1. Field of the Invention

The present invention relates to a stabilized foam. More particularly, the present invention relates to a stabilized foam suitable for use in medical and skin contact applications, having a crosslinked closed cell polyolefin foam, at least one stabilizing layer and at least one adhesive layer.

2. Description of the Related Art

For a variety of medical and skin contact products including first-aid bandages, tapes, absorbent dressings, wound covers and closures, scar reduction therapy pads, electrode grounding pads and drug delivery patches, foam is used as the exterior layer away from the skin. A skin contact adhesive is applied to this foam to provide adhesion to the skin. Many adhesives are in use and include acrylics in hot melt, solvent solution or aqueous suspension, synthetic block copolymer and other hot melts, silicone gels and silicone from solvent or hot melt systems. Often such foam films are white, tan or sheer in color and are frequently perforated for air breathability. They can also be printed with a design or logo.

An alternative unstabilized polyolefin foam material is presently in limited use. Other existing foams generally used in this application are typically vinyl or PVC based and when manufactured are cast on a release liner. This release liner provides stability to the foam while in the adhesive coating operation and possibly subsequent converting operations. The release liner can also be embossed which imparts the pattern to the foam being cast upon it.

There are several disadvantages to the use of PVC foams. PVC or vinyl foams have a plasticizer content that is inherent to the manufacturing process of PVC foam. These plasticizers have been investigated for possible medical safety risk with a concern of migration from the foam into the skin. The plasticizers in PVC also can migrate from the foam into the adjacent adhesive and/or release liners. There are regulatory limits to the use of PVC in Japan; similar restrictions are reportedly under consideration in Europe. PVC foams and films are under elevated safety scrutiny and medical device designers are receptive to alternative products.

Additionally, when bandages and tapes utilizing PVC foam are sterilized or simply aged, shrinkage of the foam is often observed. This shrinkage can be minor and is generally considered to be only a visual problem. But it can also be a more severe problem that can cause finished product rejections and/or can cause a visible exposed adhesive edge resulting from the PVC foam shrinking while the adhesive layer remains stable. The larger the die cut product, the larger the shrinkage is. Shrinkage in the PVC foam can also cause curling or rolling of the finished product. Shrinkage of any degree is not desired.

The plasticizer used in the PVC can also limit the selection of fillers and "actives" that could potentially be incorporated into or on the foam. Additionally, via a process known as "plasticizer migration" the PVC plasticizer can flow to adjacent materials and effectively limits what materials and adhesives can be adjacent to it. A typical problem is softening and expansion, even wrinkling, of an adjacent layer. Conversely, the PVC foam can absorb and "wick" oils and plasticizers into it from certain adhesives, especially hot melt adhesives containing oils. When this occurs, the PVC foam grows and changes shape over time.

Polyolefin (PO) foam is an alternative to PVC foam. This material is relatively low cost and can be manufactured in large volumes. However, it also has several undesirable properties. Polyolefin foams tend to be stiff and rigid when flexed and are easily torn or ripped. The polymers used in PO foams are cross-linked via application of electron-beam (e-beam) energy during manufacture. It is believed that this cross-linking leads to the stiffness and tearing tendency. In summary, if polyolefin foam is made to be thin and conformable, it is very weak and tears. Conversely, if thickness or density is increased to decrease tearing, the foam is stiff and not conformable to the skin.

Stiffness is generally not a desired property for foam used in a skin contact application. Flexibility and conformability are desirable properties to facilitate movements, such as, the flexing of finger, wrist, or elbow joints. Thus, despite the presence of an adhesive layer, stiff foams do not remain attached during flexing and, as a result, tends to lift off the skin.

Resistance to tearing is also critical. Of particular concern is the tearing when the foam is stressed in the cross-machine (CD) direction. Through polymer orientation in the manufacturing process, strength is concentrated in the machine direction (MD). Although strong in the machine-direction, so is the tendency to tear. For many potential end-use applications, this pronounced tear is a problem. Ideally, balanced stretch and tear properties are desired. First-aid bandages, tapes, wound covers or closures are not physically large, often ¾ inch to 2 inch at their narrow dimension. When the product is applied a degree of tension is required to attach and adhere it in place. This tension promotes tearing in PO foams. Often the PO foam is perforated to allow breathability. The physical apertures of the perforation imparted for breathability additionally weaken the foam and further promote tearing.

The low level of dimensional stability makes PO foams difficult to process through converting operations. Tensions within the unwinding pull-roll and die cutting zones result in elongation often with delayed recovery or no recovery. This tension and stretch imparted in the foam will often relax after processing and result in differential shrinkage of components and/or curling of the finished products. As thinner grades of PO foam are converted, the stretch and curling problems become exaggerated.

PVC foam has an appealing hand, good conformability and stretch recovery characteristics that make it suitable for bandages. Both PVC and polyolefin foams are economical products to manufacture.

Thus, there is a need in industry to identify alternatives to PVC and polyolefin foams that overcome these problems.

There have been efforts in recent years to locate an alternative to PVC foam to resolve the plasticizer and shrinkage problems without sacrificing the low cost or the appealing stretch/recovery properties. Alternate foams, such as, polyvinyl alcohol (PVA) foam, polyurethane foam, polyolefin foam, and the like, have also been evaluated. However, there have been no suitable alternatives found to date that meet all the design criteria listed above. The reasons for the absence of suitable alternatives include the following:

(1) polyvinyl alcohol foams are difficult to manufacture and not readily commercially available;

(2) polyurethane foams offer good physical properties but are very expensive;

(3) silicone foams also offer good properties but are more costly than the polyurethanes; and (4) although polyolefin foams are relatively low cost, they have poor dimensional stability, exhibit stretching especially when thin and tend to rip or tear when stressed, particularly when a bandage is removed from a wound. Thus, because of their stiffness, polyolefin foams generally have poor adhesion to the skin and are not conformable to the skin when flexed.

The stabilized polyolefin foam according to the present invention provides an attractive and economical alternative to PVC and other foams.

SUMMARY OF THE INVENTION

It is an object of the present invention to provide a stabilized foam that exhibits softness and conformability properties approaching or even exceeding those of PVC.

It is another object of the present invention to provide a method of preparing such a stabilized foam.

It is still another object of the present invention to provide a stabilized foam that is suitable for use in both medical and skin contact applications.

It is yet another object of the present invention to provide stabilized foam wherein the adhesive layer can be applied as a solvent-based, aqueous hot melt or co-extruded adhesive.

It is yet another object of the present invention to provide a stabilized foam that exhibits improved stability while resisting stretching when transported through slitting, perforating, die cutting, lamination, packaging or subsequent processing operations generally known as converting operations.

It is a further object of this invention to provide a stabilized foam that exhibits improved processing.

It is still a further object of this invention to provide a stabilized foam, which does not require the use of potentially hazardous plasticizers.

It is yet a further object of the present invention to provide a stabilized foam which does not have some of the disadvantages associated with PVC foams or non-stabilized polyolefin foams.

It is another object of the present invention to provide a method of treating a wound, scrape, abrasion or skin puncture.

It is still another object of the present invention to provide a method of maintaining cleanliness of an operation incision site, suture site, catheter insertion site, or an intentional skin breach site.

It is yet another object of the present invention to provide a method of monitoring electrical impulses during EKG or delivering electrical impulses in a TENS or biofeedback therapy.

It is a further object of the present invention to provide a method of softening the scar tissue and collagen deposits within a scar and reducing the raised or keloid portion of the scar over time.

These and other objects and advantages of the present invention are achieved by the use of the stabilized foam having a crosslinked closed cell polyolefin foam having a top and a bottom surface; a stabilizing layer disposed onto at least one of the top and the bottom surfaces of the crosslinked closed cell polyolefin foam; and an adhesive layer disposed onto at least one of said top and said bottom surfaces of said crosslinked closed cell polyolefin foam or onto at least one of said stabilizing layers.

Such a stabilized foam can be prepared by a method having the steps of:

providing a crosslinked closed cell polyolefin foam having a top and a bottom surface; applying a stabilizing layer onto at least one of the top and the bottom surfaces of the crosslinked closed cell polyolefin foam; and applying an adhesive layer onto at least one of said top and said bottom surfaces of said crosslinked closed cell polyolefin foam or onto at least one of said stabilizing layers.

The method of treating a wound, scrape, abrasion or skin puncture, the method of maintaining cleanliness of an operation incision site, suture site, catheter insertion site, or an intentional skin breach site, the method of monitoring electrical impulses during EKG or delivering electrical impulses in a TENS or biofeedback therapy, and the method of softening the scar tissue and collagen deposits in a scar and reducing the raised or keloid portion of the scar over time can all be achieved by employing, as needed, the stabilized foam according to the present invention.

These and other objects and advantages of the present invention can be understood by the detailed description that follows.

DETAILED DESCRIPTION OF THE PREFERRED EMBODIMENTS

The present invention provides low cost stabilized foam to the medical and first aid markets. The stabilized foam does not have any plasticizer so that no potentially harmless migration can occur.

The stabilized foam according to the present invention is heat stabilized and crosslinked so that it can resist shrinkage. The stabilized foam exhibits attractive stretch/recovery properties. Also the starting material, which is a crosslinked closed cell polyolefin foam, can be obtained directly from the manufacturer.

The crosslinked closed cell polyolefin foam is commercially available in wide widths and can be pigmented in almost any color.

The crosslinked closed cell polyolefin foam can be coated with an adhesive and can be perforated using conventional equipment to enhance breathability.

It can be produced in a variety of thicknesses and densities.

Manufacture of the Stabilized Foam

The manufacture of the "stabilized foam" is a multi-stage operation. There may be variations around this manufacturing technique however the general manufacturing process is described below.

In the first stage of the operation, a polyolefin, such as, closed cell polyolefin foam, is provided. Preferably, the closed cell polyolefin foam has a thickness about 0.010 inches to 0.050 inches and has a density about 4 pounds/cubic ft (pcf to about 20 pcf.

The closed cell polyolefin foam is prepared by extruding a mixture of polyolefin polymer(s) and a gas releasing blowing agent to produce a foam-forming mixture as a precursor thick film.

The resulting precursor foam-forming mixture is thereafter wound on a roll to form a wound foam-forming mixture in the form of a film having a thickness from about 0.0050 inches to about 0.025 inches.

The wound precursor foam-forming mixture that had been extruded to form a film is then exposed to heat in an oven, at a temperature from about 100° C. to about 250° C., whereupon the blowing agent expands to form the closed cell polyolefin foam.

The closed cell foam thus formed is exposed to a high-energy electron beam source to promote crosslinking and produce a crosslinked foam film. Other sources of crosslinking energy include gamma radiation and intense UV light.

After crosslinking, the closed cell polyolefin foam product preferably is about 0.010 to about 0.050 inches thick with a density about 4 pcf to about 8 pcf, typically about 6 pcf, and is typically pigmented to a white, tan or sheer color.

Closed cell polyolefin foams are commercially available from a variety of sources and manufacturers. Voltek and Rogers Corporation are both manufacturers of this type of foams. Closed cell polyolefin foams supplied by Voltek and Rogers and other manufacturers are suitable for use as the closed cell polyolefin foam in the method of the present invention.

Although the formation of the closed cell polyolefin foam is substantially complete at this stage, the foam is structurally weak and can tear readily, especially in the machine-direction. It is also unacceptably stiff.

While selecting the PO polymer(s) for the initial blend, a percentage of metallocene catalyzed PO polymer may be utilized. As metallocene catalyzed Polyethylene polymers are much softer and more elastic than conventional PO polymers, the resultant foam would be a softer and more conformable foam. It is recognized that via blending and mixing two or more different olefin raw materials any number of physical property modification may be achieved.

The overall composition and construction of the foam, i.e., color, density, thickness, polymer blend, or surface appearance, can be tailored to the specific end use requirements.

In the second stage of the operation, a stabilizing layer of HDPE, LLDPE, LDPE, ULDPE, metallocene catalyzed Polyethylene Polymer (mLLDPE), polyurethane, vinyl acetate, silicone gel, silicone rubber or other suitable polymer is applied onto at least one surface, i.e., the top surface and/or the bottom surface, of the crosslinked foam film and thereafter laminated or bonded onto the crosslinked foam film to stabilize the crosslinked foam film.

The stabilizing layer can be a single layer or it can be a plurality of layers, including co-extruded polymers.

Preferably, the stabilizing layer is a thin layer having a thickness from about 0.0005 inches to about 0.005 inches.

The stabilizing layer can be pressed against an embossed or patterned surface while molten to impart a permanent surface appearance in the coating.

In the practice of the method of the present invention, the stabilizing layer is adhered onto the crosslinked foam by a variety of techniques, including techniques, such as, adhesive, thermal, radio frequency, ultrasonic, electrostatic attraction and chemical bonding.

It has been found that if a layer of HDPE, LLDPE, LDPE, ULDPE, metallocene catalyzed PE polymer (mLLDPE) polyurethane, vinyl acetate, silicone gel or silicone rubber is present, i.e., is adhered to the foam, the tensile, tear and stretch/recovery properties are greatly improved. The stabilizing layer is generally extrusion coated onto the foam. The polymer(s) are processed through conventional screw extruders, slot extrusion dies and nip rollers are used during this process.

Additionally, this stabilizing layer provides a good base upon which to anchor the pressure sensitive adhesive (PSA) materials. Foam tearing and delamination routinely observed with conventional olefin foams is mitigated via the use of a stabilizing layer.

The stability imparted by this stabilization technique also enhances the ability to process the stabilized foam through printing, impregnation, die cutting, lamination and similar converting processes.

The properties of the stabilizing layer and the foam complement each other such that the presence of a stabilizing layer on the crosslinked foam film stabilizes the overall stabilized foam. By adding a stabilizing layer to the crosslinked foam film, properties comparable to those of PVC foam can be achieved without the disadvantages associated with PVC foams. Thus, the stabilizing layer provides strength to the foam allowing a thinner and softer foam to be utilized while achieving desired physical properties.

The preferred stabilizing layer has a thickness from about 0.0005 inches to about 0.0025 inches and is an extrusion coating of a polyolefin or metallocene PE film.

The composition of the stabilizing layer can be tailored to the specific end use requirements.

In the third stage of the operation, pressure sensitive adhesive (PSA) materials are introduced onto at least one layer. Several adhesive alternatives are generally available. Acrylic adhesives in a solvent that is removed via the application of heat, acrylic adhesives in an aqueous solution that are also dried via the application of heat or Hot Melt adhesives that are melted and applied via roll coating, extrusion or slot dies or pattern coating. Silicone adhesives are also available in solvent, hot melt and two-part reactive versions.

Hot melt adhesives are solvent-free adhesives that are characteristically solid at temperatures below about 180° F., are low viscosity fluids above 180° F., and rapidly set upon cooling.

A variation of the hot melt adhesive application involves the co-extrusion of the adhesive layer at the same time the stabilizing layer is applied. This saves time and cost and also minimizes any potential for delamination of the adhesive.

The effective amount of PSA material is about 20 gsm to 80 gsm and is adjusted to match the requirements of the final application. More preferably, the effective amount PSA material is about 30-70 gsm.

Should a silicone gel or rubber be used as the adhesive layer, the thickness and weight can be far greater. Thicknesses of 0.007 to 0.050 are generally preferred.

The side of the stabilized foam to which adhesive will be applied is corona treated for improved anchorage or adhesion of the adhesive layer to the stabilized foam. Corona treating is a widely used process by which electrically charged plasma is generated and exposed to a surface. The plasma disrupts and "etches" the treated surface and makes available bonding sites for attachment of the adhesive.

The adhesive can be either directly or indirectly coated onto a stabilized layer or a non-stabilized layer.

The preferred adhesives include 100% solids hot melt adhesives, such as those supplied by HB Fuller, Henkel, ATO Findlay and others.

The heated adhesive is typically delivered to a slot die using an extruder and/or a gear pump and the adhesive is cast onto, for example, about 42-lb/ream silicone coated Kraft paper at an adhesive thickness from about 0.0015 inches to 0.005 inches.

In the indirect coating process, the stabilized foam, which includes the foam and the stabilizing layer, is then squeezed into this adhesive layer. When the foam and liner are peeled apart, the adhesive remains attached to the foam substrate, not the release liner.

In this approach, adhesive application speeds of over 200 fpm and up to 600 fpm are typical.

In the direct coating process, the adhesive layer is placed directly onto the stabilized foam, which includes the foam and the stabilizing layer, and thereafter the top surface of the stabilized foam is optionally further coated with an additional adhesive layer and liner if required.

Typically, the stabilized foam and adhesive laminate described above utilizes a release liner, typically silicone coated paper or film. However, if a silicone gel or silicone adhesive is used, the use of a release liner is optional as a self-wound product is possible without a release liner because the polyolefin foam is non-adherent to, acts as, a release liner to the silicone gel or silicone adhesive.

Optionally, a patterned or discontinuous adhesive coating can also be applied onto the stabilized foam.

Perforation of the film/foam/adhesive laminate is often desired for improved breathability. Both hot needle and ultrasonic perforations are suitable and work well with these materials. Perforation can occur before adhesive coating or after. An alternate technique involves making small cuts or slits into the foam to allow airflow. Depending on the length, orientation and frequency of these slits, when pulled, the foam can physically expand and not only allow airflow but also a large degree of physical elongation. These slits would generally be made on the foam structure after the stabilizing and adhesive layers are applied.

Adhesive coated stabilized foam is often perforated and slit to narrow widths in the ¾ inch to 4 inch range. These slit rolls are further processed via the application of other materials such as absorbent non-adherent pads composed of fibers or foam, "active" treated pads that may have antibacterial or antimicrobial properties and release liners. They can be wound in a roll as a tape or die cut into a shape such as a finger bandage, or 4 inch×4 inch dressing.

Additionally, the stabilized foam can be used as a substrate to cast silicone gel materials. The silicone is used as a soft adhesive while the stabilized foam delivers the physical structure required for handling and use of the final product.

The stabilized foam is thermoformable and can be molded into a shape or additionally laminated to a substrate. The selection and thickness of the polymer used in the stabilizing layer can play an important roll in the properties of the structure following thermoforming. For example, a low melt point ethylene that can optionally contain a percentage of vinyl acetate polymer can be used both as the stabilizing layer and as a bonding layer to provide adhesion to an adjacent substrate.

Further advantages of present invention include:

(1) the stabilized foam according to the present invention exhibits properties generally comparable to those of PVC;

(2) the stabilized foam according to the present invention exhibits minimal shrinkage when sterilized or kept in storage;

(3) the stabilized foam according to the present invention is suitable for use in skin contact applications;

(4) the adhesive layer in the stabilized foam according to the present invention can be applied as a solvent-based, aqueous, hot melt, extruded or co-extruded adhesive or silicone gel;

(5) the stabilized foam according to the present invention does not require the use of plasticizers which, if present, can migrate out of the foam onto the skin, adhesive or liner and cause a potential health hazard;

(6) the stabilized foam according to the present invention offers increased dimensional stability and strength thereby allowing easier handling and processing;

(7) the stabilized foam according to the present invention allows the treatment of a patient's wound, scrape, abrasion or other skin puncture with a foam finger bandage, butterfly dressing, tape or other protective device without the need for PVC foam while maintaining acceptable conformability properties;

(8) the stabilized foam according to the present invention allows a method of treating a patient's operation incision site, suture site, catheter insertion point, or other intentional skin breach with a shower water block system to maintain incision cleanliness while the patient washes or is in hydrotherapy. Such adherent water block dressings are physically large enough to completely cover the affected area and withstand the physical demands of washing, showering and swimming; and (9) the stabilized foam according to the present invention allows a method of patient treatment utilizing electrical grounding pads designed to monitor electrical impulses (EKG pads) or to deliver electrical impulses (transcutaneous muscle stimulation (TENS) or biofeedback therapy) with a foam device without the use of PVC foam while maintaining acceptable conformability properties.

The present invention also provides a method of treating a wound, scrape, abrasion or skin puncture in a patient. The method includes the step of contacting the wound and a first-aid foam finger bandage dressing, butterfly dressing or tape having a stabilized foam according to the present invention. The stabilized foam can further have an absorbent, non-adherent and/or antimicrobial fibrous pad placed toward the wound for cleanliness, comfort and infection control. This method can be used without the need for PVC foam while maintaining acceptable conformability properties.

The present invention further provides a method of maintaining cleanliness of an operation incision site, suture site, catheter insertion site, or an intentional skin breach site in a patient. The method includes the step of treating the site with a shower water block system having stabilized foam according to the present invention.

Such adherent water block dressings are physically large enough to completely cover the affected site and effectively block the penetration of water while used in showering, washing and swimming.

The method can further employ an absorbent, non-adherent and/or antimicrobial fibrous pad placed toward the wound for cleanliness, comfort and infection control.

The present invention still further provides a method of monitoring electrical impulses in a patient during EKG or delivering electrical impulses to a patient in a TENS or biofeedback therapy. The method includes the step of treating the patient with a foam electrical grounding pad or a foam device having stabilized foam according to the present invention.

This method treats a patient with foam electrical grounding pads designed to monitor electrical impulses (EKG pads) or to deliver electrical impulses (TENS or biofeedback therapy) with a foam device without the use of PVC foam while maintaining acceptable conformability properties via the use of such stabilized foam. For patients with sensitive skin, a soft and easy-peel adhesive can be utilized.

The present invention still further provides a method of softening the scar tissue and collagen deposits in a scar and reducing the raised or keloid portion of the scar over time. The method includes the step of treating said scar with stabilized foam according to the present invention.

Preferably, the adhesive layer in the stabilized foam is a silicone gel, which can produce a reduction in the visibility of the scar. The stabilized foam provides softness and stability required by the silicone gel and allows a therapy to treat the scar for a reduction of visibility.

Typically, the silicone gel is cast or adhered onto one surface of the foam, which is then cut, if required, to the required shape to cover the scar.

The silicone gel layer can further have at least one active selected from at least one vitamin and at least one antimicrobial for assisting in maintaining skin health. Preferably, the stabilized foam is cut to a shape and size sufficient to cover the scar.

The stabilized foam according to the present invention provides an attractive alternative to adhesive coated PVC foams that are suitable for use in the medical adhesive coated foam markets.

The Examples that follow are illustrative of the present invention. They should not be construed as being limiting in any manner.

EXAMPLE 1

A cross-linked closed cell polyolefin foam sourced from Voltek, a division of Sekisui America Corporation. The foam is a 6-lb/cubic foot density foam that is extrusion coated with a linear low density polyolefin (LLDPE) stabilizing layer on one side. The color is a medium tan or "flesh" color and the total foam thickness is 0.023 inch. This extrusion coating is 0.002 inch thick and is corona treated to assist in firm anchorage of the adhesive layer. Following extrusion coating, the combined thickness is approximately 0.025 inch. The release liner is a 42-lb/ream bleached Kraft paper, available from SilTech division of Technicote, which has been coated with a silicone release coating on one side. The adhesive is a conventional block copolymer synthetic rubber hot melt from HB Fuller and is applied via a melter and gear pump that delivers the adhesive to a slot coating die. The die is from May Coating and it is set up for direct contact or proximity coating against the silicone liner.

The adhesive is melted to 350° F., pumped to the die and extrusion applied onto the silicone side of the release liner at 0.002 inches at about 250 fpm. The liner with adhesive and the stabilized foam are joined together with a set of nip rolls and wound into a roll.

Additional processing typically involves ultrasonic perforation, slitting to width, lamination to other materials and die cutting. The end use is a first aid finger bandage or dressing. Packaging is generally cohesive coated paper or for larger sizes, medical pouches using combinations of coated Tyvek, coated paper or film.

EXAMPLE 2

Cross-linked PO foam is manufactured at 0.016 inches thick with a density of 8-lbs/cubic foot and is extrusion coated with an ultra low density polyolefin film layer at 0.0015 inch thickness. A 0.003 inch polyester film that has been coated with a fluorosilicone release coating for use with silicone adhesives is proximity coated with a Dow Corning hot melt adhesive formulated with silicone.

The stabilized foam, adhesive layer and silicone release liner are all brought together in a nip between two rollers and the adhesive transfers to the stabilized foam. The assembly is rotary die cut and is useful for EKG grounding pads.

If required for a grounding pad application, a conductive material such as carbon black, carbon film or carbon fibers can be added to the foam, stabilizing layer and/or adhesive layer. The stabilizing layer allows the production of a thin and soft foam pad with the integrity required for die cutting and converting.

If the silicone adhesive used above has been compounded with an "active" such as an antibiotic, antimicrobial, pain relieving agent, or drug such as nicotine, the end use product is essentially a "drug delivery system" or transdermal patch.

EXAMPLE 3

Cross-linked PO foam is manufactured at 0.031 inches thick with a density of 6-lbs/cubic foot and is extrusion coated with a LLDPE film layer at 0.002 inch thickness. A liquid acrylic adhesive in a solvent, Gelva 2999 from Solutia, is reverse roll coated onto 53-lb Kraft release liner supplied by SilTech. The solvent is driven off as the coated liner travels through a heated oven. As the coated liner exits the oven, it is married to the stabilized foam with a set of rollers. Following slitting to width and perforation via the hot needle system, the laminate is converted into finger bandages and tape.

EXAMPLE 4

Cross-linked PO foam is manufactured at 0.023 inches thick with a density of 6-lbs/cubic foot and is extrusion coated with a HDPE film layer at 0.002 inch thickness. Either side can be treated with an adhesion promoter, such as Tyzor sold by DuPont.

The stabilized foam is processed through a horizontal oven with the treated side facing upwards. A mixture of two-part silicone elastomer, Dow Corning, is prepared and coated onto the treated side with a thickness of 0.005 inch thick. The assembly is processed through a heat tunnel oven with a 3-minute dwell at 225° F. The silicone components thermally react and cure to form a very soft and gel-like coating.

A fluorosilicone coated polyester film is used as a release liner and for protection of the silicone gel surface. This coating adheres to the skin with gentle adhesive action and is easily removed, even from hair.

This product can be slit and die cut into large pads or covers that may incorporate an absorbent pad positioned as an island on the dressing leaving an exposed adhesive edge to bond to skin. Dressings or covers of this design are used to protect a wound, incision, tube or port in the skin from contact with water while taking a shower or in Hydrotherapy. Typical sizes range from 4 inch×4 inch to 12 inch×16 inch with rectangular or rounded corners. This product is durable and can be washed in water to clean and reused.

EXAMPLE 5

A product identical to the above example is made with the silicone gel elastomer coating produced at 0.025 inch with a fluorosilicone liner. Following die cutting and packaging, the silicone gel is used as scar therapy or treatment for the reduction of visibility of hypertropic or Keloid scars. The use of silicone gel for this application is well accepted however the use of stabilized foam allows both a cost reduction, when compared to silicone gel coated onto a silicone rubber or urethane films, and a pleasing appearance of the product. The conformability and flexibility of the foam is useful in this application.

It should be understood that the foregoing description is only illustrative of the present invention. Various alternatives and modifications can be devised by those skilled in the art without departing from the present invention. Accordingly, the present invention is intended to embrace all such alternatives, modifications and variations that fall within the scope of the appended claims.

What is claimed is:

1. A method of treating a wound, scrape, abrasion, or skin puncture comprising:
  applying a stabilized foam to said wound, scrape, abrasion, or skin puncture, wherein said stabilized foam comprises:
    a cross-linked, closed cell polyolefin foam layer having a top surface and a bottom surface;
    a stabilizing layer disposed on said top surface of said cross-linked closed cell polyolefin foam layer, wherein said stabilizing layer improves one or more of the tensile, tear, and stretch/recovery properties of said polyolefin foam layer, thereby providing strength and stability to said polyolefin foam layer, wherein said stabilizing layer is not an adhesive layer; and an adhesive layer disposed on either said stabilizing layer or said bottom surface of said polyolefin foam layer, said adhesive layer being substantially flat; and applying said adhesive layer directly to a skin surface of a human body.

2. The method according to claim 1, wherein said stabilizing layer further comprises a top surface and a bottom surface and an effective amount of at least one pressure sensitive adhesive material that is disposed on said top surface and/or said bottom surface of said stabilizing layer.

3. The method according to claim 2, wherein said effective amount of said pressure sensitive adhesive material is about 20 grams per square meter (gsm) to about 70 gsm.

4. The method according to claim 1, wherein said cross-linked, closed cell polyolefin foam layer has a thickness of about 0.01 inches to about 0.05 inches.

5. The method according to claim 4, wherein said cross-linked, closed cell polyolefin foam layer has a density of about 4 pounds per cubic foot (pcf) to about 8 pcf.

6. The method according to claim 1, wherein stabilizing layer is laminated, bonded or adhered to the cross-linked, closed cell polyolefin foam layer.

7. The method according to claim 1, wherein said adhesive layer is a silicone adhesive or a silicone gel, and wherein said adhesive layer is about 0.005 to about 0.050 inches thick.

8. The method according to claim 1, wherein said adhesive layer is in the form of a zone coat, patterned, or discontinuous adhesive coating.

9. The method according to claim 1, wherein said stabilized foam further comprises an absorbent, non-adherent and/or antimicrobial fibrous pad positioned to contact said wound, scrape, abrasion, or skin puncture for exudate absorbency, cleanliness, comfort, reduction of bacterial exposure, and infection control.

10. The method according to claim 1, wherein said stabilizing layer has a thickness of about 0.0005 inches to about 0.005 inches.

11. The method according to claim 1, wherein said stabilized foam allows breathability.

12. A method of treating a wound, scrape, abrasion, or skin puncture comprising:
applying a stabilized foam to said wound, scrape, abrasion, or skin puncture, wherein said stabilized foam comprises:
a cross-linked, closed cell polyolefin foam layer having a top surface and a bottom surface;
a stabilizing layer disposed on said bottom surface of said cross-linked closed cell polyolefin foam layer, said stabilizing layer having a top surface and a bottom surface, wherein said stabilizing layer improves one or more of the tensile, tear, and stretch/recovery properties of said polyolefin foam layer, thereby providing strength and stability to said polyolefin foam layer, and wherein said stabilizing layer is not an adhesive layer; and
an adhesive layer disposed on said bottom surface of said stabilizing layer, said adhesive layer being substantially flat; and
applying said adhesive layer directly to a skin surface of a human body.

13. The method according to claim 12, wherein said cross-linked, closed cell polyolefin foam layer has a thickness of about 0.01 inches to about 0.05 inches.

14. The method according to claim 13, wherein said cross-linked, closed cell polyolefin foam layer has a density of about 4 pounds per cubic foot (pcf) to about 8 pcf.

15. The method according to claim 12, wherein said stabilizing layer has a thickness of about 0.0005 inches to about 0.005 inches.

16. The method according to claim 12, wherein said stabilized foam allows breathability.

17. A method of monitoring electrical impulses in a patient during EKG or delivering electrical impulses to a patient in a TENS or biofeedback therapy comprising:
treating said patient with a foam electrical grounding pad or a foam device having a stabilized foam, wherein said stabilized foam comprises:
a cross-linked, closed cell polyolefin foam layer having a top surface and a bottom surface;
a stabilizing layer disposed on said top surface of said cross-linked closed cell polyolefin foam layer, wherein said stabilizing layer improves one or more of the tensile, tear, and stretch/recovery properties of said polyolefin foam layer, thereby providing strength and stability to said polyolefin foam layer, wherein said stabilizing layer is not an adhesive layer; and
an adhesive layer disposed on said top surface of said polyolefin foam layer, said adhesive layer being substantially flat; and applying said adhesive layer of said stabilizing foam of said foam electrical grounding pad or foam device to a skin surface of a human body.

18. The method according to claim 17, further comprising a conductive material that is added to said cross-linked closed cell polyolefin foam layer, said stabilizing layer, and/or said adhesive layer.

19. The method according to claim 18, wherein said conductive material is selected from the group consisting of carbon black, carbon film, and carbon fibers.

20. A method of softening scar tissue and collagen deposits in a scar, and reducing visibility of a raised or keloid portion of the scar over time, comprising:
treating the scar with a stabilized foam, wherein said stabilized foam comprises:
a cross-linked, closed cell polyolefin foam layer having a top surface and a bottom surface;
a stabilizing layer disposed on said top surface of said cross-linked closed cell polyolefin foam layer, wherein said stabilizing layer improves one or more of the tensile, tear, and stretch/recovery properties of said polyolefin foam layer, thereby providing strength and stability to said polyolefin foam layer, wherein said stabilizing layer is not an adhesive layer; and
an adhesive layer disposed on said top surface of said polyolefin foam layer, said
adhesive layer being substantially flat; and applying said adhesive layer of said
stabilized foam to a skin surface of a human body.

21. The method according to claim 20, wherein said adhesive layer in said stabilized foam is a soft conformable gel.

22. The method according to claim 21, wherein said soft conformable gel is silicone gel.

23. A method of maintaining cleanliness of an operation incision site, suture site, catheter insertion site, or an intentional skin breach site comprising:
applying a stabilized foam to said operation incision site, suture site, catheter insertion site, or an intentional skin breach site, and a shower water block system, wherein said stabilized foam comprises:

a cross-linked, closed cell polyolefin foam layer having a top surface and a bottom surface;

a stabilizing layer disposed on said top surface of said cross-linked closed cell polyolefin foam layer, wherein said stabilizing layer improves one or more of the tensile, tear, and stretch/recovery properties of said polyolefin foam layer, thereby providing strength and stability to said polyolefin foam layer, wherein said stabilizing layer is not an adhesive layer; and an adhesive layer disposed on said top surface of said polyolefin foam layer, said adhesive layer being substantially flat; and applying said adhesive layer of said stabilizing foam of said water block system to a skin surface of a human body.

24. The method according to claim 23, wherein said stabilized foam further comprises an absorbent, non-adherent and/or antimicrobial fibrous pad positioned toward the operation incision site, suture site, catheter insertion site, or intentional skin breach site.

25. A method of treating a wound, scrape, abrasion, or skin puncture comprising:

applying a stabilized foam to said wound, scrape, abrasion, or skin puncture, wherein said stabilized foam comprises:

a cross-linked, closed cell polyolefin foam layer having a top surface and a bottom surface, said cross-linked closed cell polyolefin foam layer having a thickness of about 0.010 inches to about 0.031 inches;

a first stabilizing layer disposed on said top surface of said cross-linked closed cell polyolefin foam layer, said first stabilizing layer having a top surface and a bottom surface, wherein said first stabilizing layer is not an adhesive layer;

a second stabilizing layer disposed on said bottom surface of said cross-linked closed cell polyolefin foam layer, said second stabilizing layer having a top surface and a bottom surface, wherein said second stabilizing layer is not an adhesive layer; and wherein said first stabilizing layer and said second stabilizing layer improve one or more of the tensile, tear, and stretch/recovery properties of said polyolefin foam layer, thereby providing strength and stability to said polyolefin foam layer; and a pressure sensitive adhesive layer disposed on said bottom surface of said second stabilizing layer in an effective amount, said pressure sensitive adhesive layer being substantially flat; and applying said pressure sensitive adhesive layer directly to a skin surface of a human body.

* * * * *